(12) United States Patent
Mouzannar (10) Patent No.: US 9,670,457 B2
(45) Date of Patent: Jun. 6, 2017

(54) STEM CELLS AND MATRIX FROM CORD TISSUE

(71) Applicant: Stem Cell Reserve, LLC, Houston, TX (US)

(72) Inventor: Raymond Mouzannar, Houston, TX (US)

(73) Assignee: Stem Cell Reserve LP, Houston, TX (US)

( * ) Notice: Subject to any disclaimer, the term of this patent is extended or adjusted under 35 U.S.C. 154(b) by 252 days.

(21) Appl. No.: 13/890,134

(22) Filed: May 8, 2013

(65) Prior Publication Data

US 2013/0302890 A1    Nov. 14, 2013

Related U.S. Application Data

(60) Provisional application No. 61/644,423, filed on May 8, 2012.

(51) Int. Cl.
*C12N 5/0735*    (2010.01)
*C12N 5/0775*    (2010.01)

(52) U.S. Cl.
CPC ......... *C12N 5/0606* (2013.01); *C12N 5/0665* (2013.01)

(58) Field of Classification Search
None
See application file for complete search history.

(56) References Cited

U.S. PATENT DOCUMENTS

| | | | |
|---|---|---|---|
| 7,318,998 B2 | 1/2008 | Goldstein | |
| 7,775,965 B2 | 8/2010 | McFetridge | |
| 8,481,311 B2 * | 7/2013 | Davies et al. | 435/366 |
| 2005/0203636 A1 | 9/2005 | McFetridge | |
| 2006/0039896 A1 | 2/2006 | Kleinsek | |
| 2006/0223177 A1 * | 10/2006 | Harris et al. | 435/325 |
| 2009/0275127 A1 * | 11/2009 | Ennis et al. | 435/366 |
| 2010/0278783 A1 | 11/2010 | Rouy | |
| 2011/0129918 A1 | 6/2011 | Hung | |
| 2011/0151556 A1 | 6/2011 | Kallis | |

FOREIGN PATENT DOCUMENTS

WO    WO 2008060037 A1 *    5/2008

OTHER PUBLICATIONS

Ballen K., "Challenges in Umbilical Cord Blood Stem Cell Banking for Stem Cell Reviews and Reports", Stem Cell Rev and Rep (2010) 6:8-14.
Chen J., et al., "Scaffolds for tendon and ligament repair: review of the efficacy of commercial products", Expert Rev. Med. Devices (2009) 6(1), 61-73.
Martin-Rendon E., et al., "5-Azacytidine-treated human mesenchymal stem/progenitor cells derived from umbilical cord, cord blood and bone marrow do not generate cardiomyocytes in vitro at high frequencies", Vox Sanguinis (2008) 95,137-148.
Montoya C.V., et al., "Preparation of Ex Vivo-Based Biomaterials Using Convective Flow Decellularization", Tissue Engineering: Part C (2009) vol. 15, No. 2, 191-200.
Rowley J., et al., "Meeting Lot-Size Challenges of Manufacturing Adherent Cells for Therapy", BioProcess International (2012) Supplement, 16-22.
Keane T.J., et al., "Consequences of ineffective decellularization of biologic scaffolds on the host response", Biomaterials 33 (2012) 1771-1781.
Lavrentieva A., et al., "Effects of hypoxic culture conditions on umbilical cord-derived human mesenchymal stem cells", Cell Communication and Signaling (2010) 8:18.
Grayson W.L., et al., "Effects of Hypoxia on Human Mesenchymal Stem Cell Expansion and Plasticity in 3D Constructs", Journal of Cellular Physiology (2006) 207:331-339.
Kessler D.A., et al., "FDA Regulation of Stem-Cell-Based Therapies", The New England Journal of Medicine (2006) 355;16, 1730-1735.
Bieback K., et al., "Critical Parameters for the Isolation of Mesenchymal Stem Cells from Umbilical Cord Blood", Stem Cells (2004) 22:625-634.
Secco M., et al., "Multipotent Stem Cells from Umbilical Cord: Cord Is Richer than Blood!", Stem Cells (2008) 26:146-150.
Lazarus H.M., et al., "Cotransplantation of HLA-Identical Sibling Culture-Expanded Mesenchymal Stem Cells and Hematopoietic Stem Cells in Hematologic Malignancy Patients", Biology of Blood and Marrow Transplantation (2005) 11:389-398.
Mishra A., et al., "Buffered Platelet-Rich Plasma Enhances Mesenchymal Stem Cell Proliferation and Chondrogenic Differentiation", Tissue Engineering: Part C (2009) vol. 15, No. 3, 431-435.
Tibbitt M.W., et al., "Hydrogels as Extracellular Matrix Mimics for 3D Cell Culture", Biotechnology and Bioengineering (2009) vol. 103, No. 4, 655-663.
Leisten I., et. al., "3D co-culture of hematopoietic stem and progenitor cells and mesenchymal stem cells in collagen scaffolds as a model of the hematopoietic niche", Biomaterials 33 (2012) 1736-1747.
Baharvand H., et. al., "Differentiation of human embryonic stem cells into hepatocytes in 2D and 3D culture systems in vitro", Int. J. Dev. Biol. (2006) 50:645-652.
Bosch J., "Distinct Differentiation Potential of "MSC" Derived from Cord Blood and Umbilical Cord: Are Cord-Derived Cells True Mesenchymal Stromal Cells?", Stem Cells and Development (2012) vol. 21, No. 11, 1977-1988.

* cited by examiner

*Primary Examiner* — Renee Claytor
*Assistant Examiner* — David Berke-Schlessel
(74) *Attorney, Agent, or Firm* — Boulware & Valoir (57) ABSTRACT

Methods for isolating and culturing stem cells, making tissue matrix, making matrix infused with stem cells, and methods of stem cell therapy are provided.

11 Claims, 3 Drawing Sheets

STEM CELLS AND MATRIX FROM CORD TISSUE

CROSS-REFERENCE TO RELATED APPLICATIONS

This application claims priority to 61/644,423, filed May 8, 2012, and expressly incorporated by reference for all purposes herein.

FEDERALLY SPONSORED RESEARCH STATEMENT

Not applicable.

REFERENCE TO MICROFICHE APPENDIX

Not applicable.

BACKGROUND OF THE INVENTION

Stem cells are unspecialized cells that have two defining properties: the ability to differentiate into other cells and the ability to self-regenerate.

The ability to differentiate is the potential to develop into other cell types. A totipotent stem cell (e.g. fertilized egg) can develop into all cell types including the embryonic membranes. A pluripotent stem cell can develop into cells from all three germinal layers (e.g., cells from the inner cell mass). Other cells can be oligopotent, bipotent or unipotent depending on their ability to develop into few, two or one other cell type(s).

Self-regeneration is the ability of stem cells to divide and produce more stem cells. During early development, stem cell division is believed to be symmetrical i.e. each cell divides to gives rise to daughter cells, each with the same potential. Later in development, stem cells are believed to divide asymmetrically with one of the daughter cells produced being a stem cell and the other a more differentiated cell.

Stem cells are further classified according to their differentiation potential, roughly as follows:

As development proceeds, there is a loss of potential and a gain of specialization, a process called determination. For example, the cells of the germ layers are more specialized than the fertilized egg or the blastomere. The germ layer stem cells give rise to progenitor cells (also known as progenitors or precursor cells). For example, a cell in the endoderm gives rise to a primitive gut cell (progenitor), which can further divide to produce a liver cell (a terminally differentiated cell).

While there is consensus in the literature that a progenitor is a partially specialized type of stem cell, there are differences in how progenitor cell division is described. For instance, according to one source, when a stem cell divides at least one of the daughter cells it produces is also a stem cell; when a progenitor cell undergoes cell division it produces two specialized cells. A different source, however, explains that a progenitor cell undergoes asymmetrical cell division, while a stem cell undergoes symmetrical cell division.

The different kinds of human stem cells identified to date include: embryonic stem cells derived from embryos artificially produced in in-vitro fertility clinics, fetal stem cells derived from aborted fetuses, umbilical cord blood and placental blood stem cells, umbilical cord and placental tissue stem cells, bone marrow blood stem cells, peripheral blood stem cells, bone marrow mesenchymal stem cells, adult fat or adipose tissue-derived stem cells, cardiac muscle stem cells, skin epidermis stem cells, endothelial progenitor cells, brain and spinal cord derived neural stem cells, dental pulp stem cells and olfactory epithelium stem cells. In addition, human embryonic-like stem cells can be synthetically manufactured by inducing any adult terminally differentiated cell like a cheek skin fibroblast or even an adult stem cell into an embryonic-like stem cell.

Stem cells of the umbilical cord tissue are defined as mesenchymal stem cells or stromal stem cells with set characteristics. However, not all umbilical cord tissue cells have been tested for stem cell activity. Cord tissue mesenchymal stem cells have an ability to adhere to laboratory flask or dish surfaces and their morphology is fibroblast-like. They express specific surface markers like CD105, CD133, CD166, CD44, CD54, CD90, HLA-ABC, CD146, CD73, STRO-1 and are capable of differentiating into chondrocytes, adipocytes and osteocytes. Cord tissue mesenchymal stem cells are expected to engraft better than bone marrow

| Differentiation Potential | Number of cell types | Example of stem cell | Cell types resulting from differentiation |
|---|---|---|---|
| Totipotential | All | Zygote (fertilized egg), blastomere | All cell types |
| Pluripotential | All except cells of the embryonic membranes | Cultured human ES cells | Cells from all three germ layers |
| Multipotential | Many | Hematopoietic cells | skeletal muscle, cardiac muscle, liver cells, all blood cells |
| Oligopotential | Few | Myeloid precursor | 5 types of blood cells (Monocytes, macrophages, eosinophils, neutrophils, erythrocytes) |
| Quadripotential | 4 | Mesenchymal progenitor cell | Cartilage cells, fat cells, stromal cells, bone-forming cells |
| Tripotential | 3 | Glial-restricted precursor | 2 types of astrocytes, oligodendrocytes |
| Bipotential | 2 | Bipotential precursor from murine fetal liver | B cells, macrophages |
| Unipotential | 1 | Mast cell precursor | Mast cells |
| Nullipotential | None | Terminally differentiated cell e.g. Red blood cell | No cell division | mesenchymal stem cells or blood stem cells because unlike bone marrow mesenchymal stem cells and cord blood stem cells, they do not express a mature set of major histocompatibility antigens.

However, there are also inconsistencies in how stem cells are described and/or identified, making the field a challenging one to understand, and the literature is replete with inconsistencies.

The ability of stem cells to self-renew and give rise to subsequent generations with variable degrees of differentiation capacity offers significant potential to replace diseased and damaged areas in the body, with minimal risk of rejection and side effects. Many medical researchers believe that stem cell treatments have the potential to change the face of human disease and human tissue degeneration. Although unidentified back then, stem cells were used in tribal medicine thousands of years ago when tribe medical leaders looked for "young" blood to treat sick tribe members that would be regarded today as consanguineous people.

A number of stem cell therapies already exist, but most are at experimental stages or costly, with the notable exception of bone marrow and cord blood transplantations. Medical researchers anticipate that adult and embryonic stem cells will soon be able to treat cancer, Type 1 diabetes mellitus, Parkinson's disease, Huntington's disease, Celiac Disease, cardiac failure, muscle damage and neurological disorders, and many others. Nevertheless, before stem cell therapeutics can be applied in the clinical setting, more research is necessary to understand stem cell behavior after processing and upon transplantation as well as the mechanisms of stem cell interaction with the diseased/injured microenvironment.

Stem cells of different differentiation potentials are also defined by their source, age and method of preparation. For example, young cells are better in quality than old cells. Alternatively, cord blood is a better source of blood stem cells than bone marrow. On the other hand, time in culture, presence or lack of other cells in culture, xenogeneic or synthetic supplements and reagents alter biological properties of cells and stem cells including gain or loss of functions or specific properties like proliferation and differentiation potential.

In addition, for stem cells to be used in regenerative medicine one must consider two things, safety and efficacy. The method of preparation of cells and tissues for transplantations is very important because manipulating cells and tissue and introducing them to new agents, reagents and environments may turn these cells harmful or inefficient when transplanted in any individual, self or not. Further, current culture methods change stem cells in ways that can reduce or eliminate their efficacy and compromise their safety. Indeed, cord blood transplantation professionals complained about quality of cord blood units they receive from public and private banks and expect to transplant into patients as cord blood processing was not standardized and regulated by the US FDA. It was not until 2011 that cord blood became a licensed biological product. Except bone marrow and cord blood, all other cellular products remain in experimental stage and there is currently no FDA processing standard in place.

Methods to collect and preserve all types of stem cells fall into two basic categories—unmanipulated (or at least minimally manipulated) and manipulated methods.

The minimal manipulation method of collecting and freezing is mainly used for bone marrow and cord blood. The first minimal manipulation involved the collection of blood and direct infusion into a patient. Alternatively, aspirates of blood or marrow were mixed with blood anticoagulant and layered on specific density solutions like Ficoll-Hypaque to allow the density dependent separation of blood cells. The separation is accelerated by centrifugation. The middle "buffy coat" layer containing the blood stem cells is gently aspirated, leaving behind the top layer plasma and the bottom layer containing red blood cells. At this stage, the buffy coat is mixed with a cryoprotectant, like dimethyl sulfoxide (DMSO) or glycerol, to a final concentration of 10% and immediately slow frozen to $-120°$ C. before immersing it in the liquid or gas phase of a liquid nitrogen storage tank or Dewar.

A new version of this method involves replacing the density solution with a set of processing bags connected through tubing and placed in a special device such as the AXP or SEPAX which is spun in a centrifuge leaving three final products, a red blood cell reduced concentration of mononuclear cells (buffy coat) containing blood and other stem cells, plasma, and red blood cells.

In other minimal manipulation methods, tissues are excised from one area of the body and retransplanted back in another of the same type. For example, skin from the leg area transplanted in an injured or burnt skin in the arm or face. Another example is scraped or shaved bone from the pelvis transplanted in a fractured or missing bone in the jaw.

The manipulated methods involve manipulating the cells longer than one hour and/or mixing the cells with agents other than water, phosphate buffer solution, cryoprotectant and Ficoll-Hypaque. Typically, in these methods, mechanical sectioning and/or enzymatic digestion of tissue to separate cells is used. Cells may be sorted, transfected for gene therapy and cultured in serum free media or media containing animal or genetically non-identical human sera, or genetically non-identical platelet lysates. Growth factors like epidermal growth factor and hormones like insulin may also be added to stimulate growth and proliferation of cultured cells. Furthermore, cells may be cultured in a two-dimensional or three-dimensional matrix where they may be guided to grow into a specific form. Alternatively, a piece of extracted tissue may be decellularized to create a matrix in which autologous or allogeneic cells may be infused. The matrix containing the necessary cells can be transplanted back into a patient to regrow and heal a degenerated tissue. All of these methods have a higher risk of negatively impacting stem cell safety and efficacy.

What is needed in the art are better methods isolating, culturing and preserving stems cells, that provides a more reliable, reproducible, safer and efficacious product.

BRIEF SUMMARY OF THE INVENTION

The present invention describes a method of collection and a four way processing of human umbilical cord to manufacture decellularized human umbilical cord matrix, cryopreserve whole umbilical cord tissue products, manufacture cells from whole human umbilical cord tissue and culture those in three dimensions in media containing serum, plasma or platelet lysate derived from cord blood derived from the same genetic source, in the presence of low oxygen tension. This methodology produces a superior cell product that preserves stem cell biology, which leads to better regenerative potential in injured, diseased and aging patients or animals.

In more detail, the invention is a method of producing stem cells and tissue matrix. Preferably, the tissue preparation commences within 48 hours, preferably within 16 or 12 hours, of obtaining the tissue, and the process occurs in a class 10,000 clean room facility.

The method begins with obtaining (directly or indirectly) a tissue from an animal source and cleaning said tissue with e.g., a sterilizing agent. The tissue is then mechanically dissociated, e.g., with a blade, to produce cells and tissue fragments, preferably very thin slices or cubes of tissue, or any shape needed for the ultimate transplant use. The more surface area per unit volume, the easier it will be to mechanically dissociate the cells from the tissue matrix, hence extremely fine slices are preferred where the cells are to be retained for subsequent use.

Where decellularized matrix is desired, the tissue fragments are then chemically and/or mechanically treated to liberate or lyse additional cells, leaving a tissue matrix from which at least 70%, preferably 75%, 80%, 85%, 90% or 95%, of the cells have been removed.

The cells are then cultured and/or stored. Cells can be cultured with matrix or fragments, or separately, depending on ultimate use. Culturing is preferably via a three dimensional cell culture in 0.1% to 5% oxygen environment at 37° C. in a medium supplemented with serum, plasma or platelet lysate isolated from either said source or a genetically identical source. Preferably, the culturing step is in a humidified carbon dioxide cell culture chamber. The point of culturing the cells in a hypoxic environment is to stimulate stem cell reproduction, but inhibit the growth and reproduction of the differentiated cells. Three-dimensional culturing also provides a more natural environment, and minimizes the cellular changes that can occur on culturing. Further, the addition of tissue fragments or matrix provides an environment that more closely mimics the in vivo environment.

The starting tissue can be any tissue from the body that contains some stem cells, and preferably includes skin, umbilical cord, heart, brain, or hair. However, body fluids such as urine, blood and the like can also be used. A preferred tissue is whole umbilical cord tissue, which can contain more or less cord blood.

The tissue matrix, fragments and the cells can be used immediately or stored for future use, and they can be stored either together or separately, again depending on the ultimate use. Storage can be by freezing, e.g., with a cell protecting agent such as DMSO or glycerol, but the tissue matrix can be freeze dried or lyophilized as well, and rehydrated for use according to known techniques.

Importantly, the method produces a mixture of differentiated cells, stem cells and progenitor cells. These can be used as is, or used by first re-infusing back into a tissue matrix. The stem cells can also undergo further separation and amplification, but we specifically contemplate using a mixture of cells in therapeutic applications. The mixture of cells provides a more natural environment, and the stem cell can respond to signals from the other cells and/or the matrix to stimulate differentiation into the desired cell type.

When used together with a matrix, the matrix can be from the same or a genetically identical animal, or can be from a different animal, since the matrix is largely decellularized and the matrix itself will be minimally antigenic. The matrix provides the cells with a scaffold for growth, as well as the needed growth factors and the like, ensuring a highly safe and effective, biocompatible tissue replacement.

Another embodiment is a method of cell therapy, wherein a mixture of differentiated cells, stem cells and progenitor cells are reinfused into a tissue matrix, and said reinfused tissue matrix is implanted into a patient in need thereof. Preferably, the cells are derived from umbilical cord tissue, or from cord tissue and cord blood.

Another embodiment is a method of cell culture, wherein a mixture of differentiated cells, stem cells and progenitor cells from a patient are cultured in a hypoxic environment in a medium supplemented with serum, plasma or platelet lysate isolated from said patient or a genetically identical patient. Preferably, culturing is via three-dimensional culture, and also preferably there is co-culture with tissue fragments.

Other embodiments of the invention are methods of stem cell therapy, using one or more of the products and/or methods described herein.

There are substantial differences between the invention as described and claimed herein and the prior art methodologies. These are elaborated on below.

1. The facility in which the procedure is executed should be a dedicated clean room with positive air-flow. The clean room facility is made of at least three zones, the actual clean room where processing occurs (preferably class 10,000), as well as a gowning room (preferably class 10,000), and an entry airlock room (preferably class 10,000 or 50,000 or more). Preferably, the facility also has sample receiving rooms, diagnostic rooms (for performing tests for infectious disease, and the like), and final sample storage rooms, as well as pass-through hatches for samples to pass to each next processing zone.

By class 10,000 compliant, what is meant that the facility at least complies with the US FED STD 209E regulations or equivalent. Also, preferably the facility is a dual process facility, with separate but mirrored facilities for public and private stem cell processing and banking facilities. A preferred facility is described in Ser. No. 13/555,187, filed Jul. 22, 2012, and incorporated herein by reference in its entirety.

2. The method uses tissues to produce stem cells, in particular cord tissue, instead of the usual cord blood samples, although of course cord tissue may contain some amount of blood.

3. The tissue is CUT to a certain shape (without separating vessels from rest of tissue) before producing a matrix of the desired shape, devoid of cells, without using nucleases or other enzymes, as described in US20050203636, U.S. Pat. No. 7,775,965, and U.S. Pat. No. 7,318,998.

4. In the initial culturing, the method is not focused on specific cell types (such as mesenchymal stem cells or endothelial stem cells), nor on using cell suspensions to culture the cells, as described in US20110129918. Instead, the cells are grown as a mixture, again providing a more natural culture environment.

5. Blood components (serum, plasma, platelet lysate) derived from the tissue source (or a genetically identical source) are used to culture the cells with or without the matrix above. The use of autologous serum or components is described in US20100278783 and US20060039896, and thus is not by itself novel. However, autologous blood or tissue components have NOT been used for allogeneic stem cell preparation. In other words, whereas prior art isolates or prepares cells from a tissue source using blood and tissue components derived from unrelated allogeneic or synthetic sources before transplanting said cells into another allogeneic third party being an animal or human, this invention isolates or prepares cells using blood and tissue components derived from the same source before transplanting these cells into same or unrelated allogeneic third party being an animal or human. Accordingly, using components derived from the same source of cells leads to lower risks of transmitting disease and a more natural and better environment for cell maintenance, growth, differentiation, proliferation and transplantation. For example, serum and platelets will contain natural amounts of growth factors and cytokines necessary to maintain the cells in their natural cross talk environment being either a undifferentiated state or a state of response to differentiation factors. In addition to making the product more potent, using autologous components and reducing foreign agents in cell culture media during biological preparations like stem cell processing is more accepted by the scientific community and more importantly by the US FDA that eventually reduces time to market these biologicals.

6. The cells are grown in 3D (e.g., in a mini bioreactor). Three dimensional culture techniques have been applied to stem cell culturing. Gerlach J C, et al., Dynamic 3D culture promotes spontaneous embryonic stem cell differentiation in vitro, Tissue Eng Part C Methods. 2010 February; 16(1): 115-21. However, culturing or co-culturing cells in a bioreactor, in or on a three dimensional surface derived from the genetic source is novel and expected to lead to maintenance or enhancement of one or more of their biological properties. When it comes to stem cells, it is important to preserve their differentiation potential in response to stimuli. 3D culturing on matrices or scaffolds derived from the same cell source is expected to enhance the usefulness of the cells when transplanted alone or when transplanted in combination with the matrix or scaffold. Preserving physical property of the matrix or scaffold provides cells with a surface that is appropriate for their migration, proliferation or differentiation on or within the matrix.

7. Stem cells are cultured in a hypoxic environment. Normally cells are transferred directly from a normoxic to a hypoxic environment. This invention uses cells that are gradually or suddenly exposed to a hypoxic environment ranging from 0.5% to 7% oxygen while cultured in or on a 3D matrix in the presence or absence of 1% to 10% autologous blood components in an incubator at 37 degrees for 0 to 14 days. These conditions lead to a novel biologically active cellular product useful for transplantation and regenerative medicine.

8. The stem cells in combination are reinfused into the acellular matrix. Specific cells derived from the animal or human, alone or in different combinations are reinfused at a specific density of 50,000 to 600,000 cells per cubic centimeter of a piece of vascularized or avascularized tissue that has been decellularized. For cell combination, for example a 5 to 1 ratio of mesenchymal stem cells to endothelial progenitor cells are infused in a decellularized piece cord tissue and incubated under conditions mentioned above.

8. The stem cells mixture is reinfused into the acellular matrix, rather than a single type of supposedly-purified stem cell.

This unique combination of steps is unobvious for several reasons:

1. Researchers are focused on using serum free media, to avoid the use of expensive and possibly contaminated serum components, esp. those derived from non-human animal sources.

2. Researchers are focused on bone marrow and adipose stem cells, not cord tissue per se.

3. Some researchers believe that cord tissue does not even contain mesenchymal stem cells (MSCs). There is inconsistency in the characterization of mesenchymal stem cells derived from cord tissue. The basis of this controversy is suggested by variability of methods used to isolate and culture and assay these cells. For example, one research group uses fetal bovine serum while another group uses serum-free medium. See Bosch J, et al., Distinct Differentiation Potential of "MSC" Derived from Cord Blood and Umbilical Cord: Are Cord-Derived Cells True Mesenchymal Stromal Cells?, Stem Cells and Development (2012).

4. Researchers use autologous components for autologous use but NOT for allogeneic use. Whereas current use of autologous serum is to culture and expand autologous cells or treatment of an autologous recipient, our invention uses autologous serum to culture and expand autologous cells before transplanting cultured cells into an allogeneic or unrelated recipient.

5. Researchers have not used autologous sera, plasma and platelet lysates for cord tissue culture.

6. Researchers use third party bone marrow MSCs to co-culture with second party cord blood MSCs before transplanting into a human or animal.

7. Researchers culture bone marrow cells, adipose tissue cells and cord tissue cells in 2D.

8. Researchers do not culture stem cells in 3D with genetically identical serum, plasma or platelet lysates.

9. Researchers do not culture in a hypoxic environment. Specifically, exposing cells to sudden or gradually reduced (from 21% oxygen down to 7%-1% oxygen pressure) oxygen levels (1-7% oxygen) leads to a better physiological state of the cells and hence transplanting cells prepared in this manner enhances their regenerative potential.

10. Researchers do not make shape specific matrices from natural sources. This invention includes repair of damaged tissue by using area and volume specific matrices that fill in or replace the specific damaged area. For example, the sterile cellularized, decellularized or recellularized umbilical cord is cut to the shape of the damaged area or volume before it is transplanted. Alternatively, patches can be manufactured by 3D printing cells derived from the umbilical cord into specific shapes corresponding to the damaged area or volume.

11. Researchers do not use non-enzymatic processes in decellularization to produce such matrices.

12. Researchers do not reinfuse the matrix with autologous or allogeneic cord blood or tissue cells.

13. Researchers do not infuse the matrix with more than one type of specific cell.

By "animal" herein what is meant is any non-human animal or human. Preferably the animals are mammals.

By "tissue matrix" herein what is meant is that at least 70% of the original cells of said tissue have been removed, leaving behind extracellular matrix (ECM) containing connective tissue, proteoglycans, such as heparin sulfate, chondroitin sulfate, and keratin sulfate, non-proteoglycan polysaccharides, such as hyaluronic acid, fibers such as collagen and elastin, and miscellaneous components such as fibronectin and laminin.

By "hypoxic" what is meant herein is that the cells are cultured with less than usual pressure of 159 mm Hg (21% $O_2$), but are not anoxic. Preferably 0.5-15% $O_2$ is used, preferably 1.5-5% $O_2$ for MSCs from umbilical cord.

By "mechanically dissociating" what is meant is physical method of reducing tissue size, e.g., by slicing or cutting, homogenizing, mortar and pestle, and the like. Preferably, the tissue is cut into fine strips or cubes with a blade.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise," "have," "include" and "contain" (and their variants) are open-ended linking verbs and allow the addition of other elements when used in a claim.

The phrase "consisting of" is a closed linking verb and does not allow the addition of any other elements.

The phrase "consisting essentially of" occupies a middle ground, allowing the addition of non material elements such as extra washes, precipitations, drying or various buffers and the like.

The following abbreviations are used herein:
GMP Good Manufacturing Practices
FDA Food and Drug Administration
DMSO Dimethylsulfoxide
DMEM Dulbecco Modified Essential Medium
SCR Stem Cell Reserve
PAA Peracetic Acid

DETAILED DESCRIPTION OF THE INVENTION

The present invention is a method of umbilical cord cell isolation and culture whereby the cord tissue is processed in a public and private GMP facility, in clean class <10,000 rooms containing class 100 or less biosafety cabinets. The FDA does not currently require the use of such clean rooms, but it is expected that this will become a requirement in the future, and even where not a legal requirement is a best practice and should be an industry standard.

In one aspect of this invention, a method of producing tissue matrix is provided, and the method comprises: a) obtaining a tissue from an animal; b) cleaning said tissue with a sterilizing agent; c) cutting or striating said tissue to produce one or more tissue fragments of a desired shape; d) mechanically or chemically treating said tissue fragments to produce a tissue matrix; and e) storing said tissue matrix.

The method can be realized by a combination of one or more of the following embodiments. In one embodiment, the method further comprises: storing said tissue matrix at −80° C., or lyophilizing said tissue matrix and storing at room temperature, or freezing said tissue matrix at −80° C. to −196° C. In another embodiment, the tissue matrix is reinfused with a mixture of differentiated cells, stem cells and progenitor cells before use. In still another embodiment, the mixture of differentiated cells, stem cells and progenitor cells is from the animal. In yet another embodiment, where the mixture of differentiated cells, stem cells and progenitor cells is from a different animal. In yet another embodiment, the tissue comprises umbilical cord.

In another aspect of this invention, a method of cell therapy is provided, wherein a mixture of differentiated cells, stem cells and progenitor cells are reinfused into a tissue matrix, and said reinfused tissue matrix is implanted into a patient in need thereof. The method can be realized by a combination of one or more of the following embodiments. In one embodiment, the tissue matrix is obtained from umbilical cord tissue. In another embodiment, the mixture of differentiated cells, stem cells and progenitor cells is obtained from umbilical cord tissue.

In still another aspect of this invention, a method of cell culture is provided, wherein a mixture of differentiated cells, stem cells and progenitor cells from a patient are cultured in a three-dimensional culture in an hypoxic environment in a medium supplemented with serum, plasma or platelet lysate isolated from said patient or a genetically identical patient. The method can be realized by a combination of one or more of the following embodiments. In one embodiment, the cells are co-cultured with tissue matrix. In another embodiment, the mixture of differentiated cells, stem cells and progenitor cells is obtained from umbilical cord tissue. In still another embodiment, the mixture of differentiated cells, stem cells and progenitor cells is obtained from umbilical cord tissue and umbilical cord blood. In yet another embodiment, the mixture of differentiated cells, stem cells and progenitor cells is co-cultured with tissue fragments. In yet another embodiment, said tissue fragments are obtained from umbilical cord tissue.

In still another aspect of this invention, a method of cell therapy is provided, wherein a mixture of stem cells from umbilical cord blood and stem cells from umbilical cord tissue are used together for cell therapy in a patient in need thereof.

In still another aspect of this invention, a method of cell therapy is provided, wherein a mixture of stem and progenitor cells from umbilical cord blood and from umbilical cord tissue are used together for cell therapy in a patient in need thereof.

In still another aspect of this invention, a method of cell therapy is provided, wherein a mixture of stem and progenitor cells from umbilical cord blood and from umbilical cord tissue are used together with autologous or allogeneic tissue matrix from cord tissue for cell therapy in a patient in need thereof.

All of the cord with its blood vessels is collected and sterilized by flushing cord vessels with sterile antibiotic and antimycotic containing calcium- and magnesium-free PBS. The cord surface is cleaned with regular alcohol swabs before placing in a sterile bag, sealed and safely placed in a temperature controlled damage resistant shipping box and shipped to Stem Cell Reserve's facility and received no more than 16 hours post delivery. At SCR's patent pending facility, private and public cord tissues are processed in designated areas in different ways.

For cryopreserving whole cord tissue, a piece of cord tissue is cut; a sterile plastic tube is inserted in the vessels to keep them distended or straight; the tissue is placed in a sterile tube filled with low glucose Dulbecco Modified Essential Medium (DMEM) or similar medium (e.g., a variety of stem cell media are commercially available) containing antibiotics and antimycotics, such as penicillin and streptomycin respectively, with or without 5-20% final concentration of serum, plasma or platelet lysate derived from cord blood of the same newborn. GMP grade DMSO is added to a final concentration of 5-10% before slow freezing to −120° C. then quarantined in the gas phase of liquid nitrogen until communicable disease diagnostics is clear. At this point, the tissue is transferred to private or public designate long-term gas phase liquid nitrogen dewars.

To manufacture an acellular matrix that can be used in the future for autologous or allogeneic purposes to support the regeneration of bone, cartilage, skin, fat, muscle, retinal, lens and nervous tissue, a piece of cord tissue is straightened by inserting a thick glass stick in the cord vessels. Then the cord tissue is decellularized with 0.1% peracetic acid (PAA) for 2 hours with mechanical agitation and subsequent 15 minute wash with phosphate buffered saline (PBS) before treating the tissue with DNAse and RNAse in calcium magnesium-free PBS at 37° C. for 1 hour. Cord tissue can also be decellularized with other chemical reagents, such as hypotonic solutions, alcohols, SDS or other detergents, Trypsin, and the like. Mechanical dissociation methods can also be used, such as convection flow, sonication, and the like.

In contrast, when the cells are to be retained, the tissue can be finely sliced, diced or homogenized and the cells gently liberated. For example, the tissue can be completely sliced into thin strips (shaved slices), or only striated partway through, and gentle rocking or convection flow applied, if needed, to free the cells from the thin piece of tissue. This method preserves the cells for subsequent use.

Cord tissue is then washed with deionized water, calcium magnesium-free PBS, and deionized water. This decellularized piece of tissue will be preserved by placing it in antibiotics and antimycotics together with 10% GMP grade DMSO containing calcium magnesium-free PBS and slowly frozen to −80° C. then placed in public or private designated freezer.

To isolate mesenchymal stem cells (along with the progenitor and differentiated cells), cord tissue is mechanically dissociated or cut within 16 hours of delivery into thin filaments (including vessel walls) using a sterile scalpel and then placed in suspension to be cultured in a prior art 3D chamber, preferably with 1-7% oxygen and a low glucose DMEM medium, preferably supplemented with either serum, plasma or platelet lysate derived from the same newborn. Blood components can also be isolated from the same person or animal later in life. Hence maintaining a source of autologous blood components as long as possible.

One week later, cells derived from this culture are collected and characterized for size, surface markers and stem cell properties using flow cytometry, reculture, and differentiation into different lineages and capacity to regenerate an animal damaged tissue. Following characterization, all cells are collected and suspended in fresh DMEM medium containing either cord blood serum, plasma or platelet lysate derived from cord blood of the same newborn. GMP grade DMSO is added to a final concentration of 10% before slow freezing to −120° C., then quarantined in the gas phase of liquid nitrogen until communicable disease diagnostics is clear. Until then, the cells or tissues are transferred to private or public designated long-term gas phase liquid nitrogen dewars.

Figure 1:
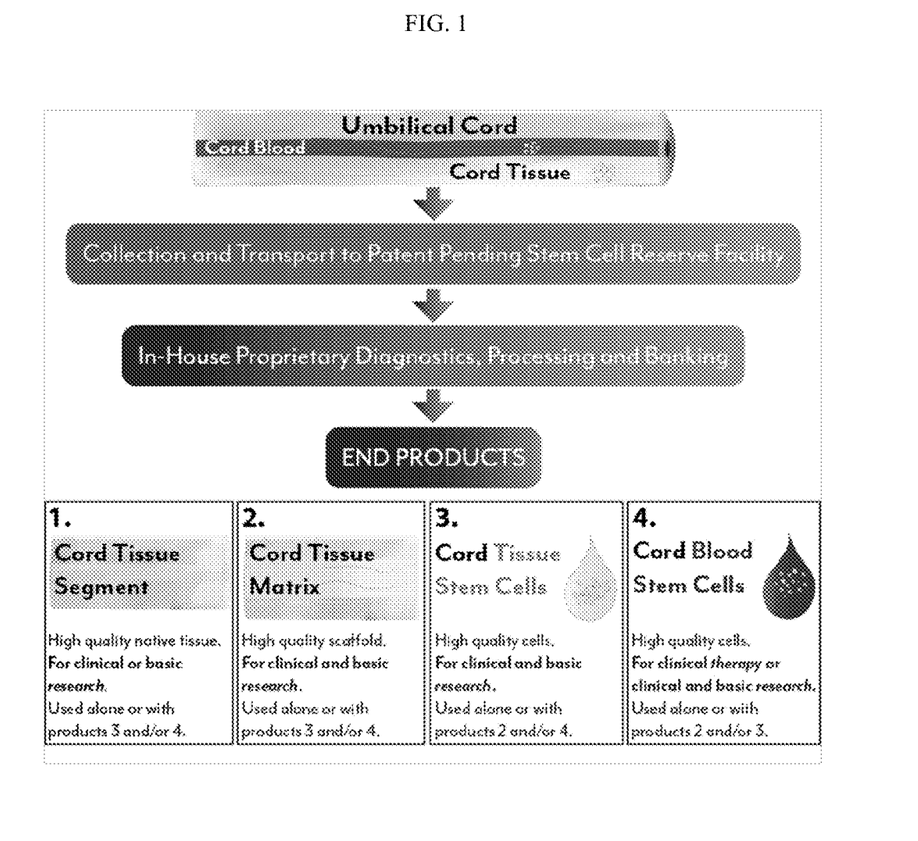
FIG. 1 shows the possible application of umbilical cord tissue collected from a patient.
Figure 2:
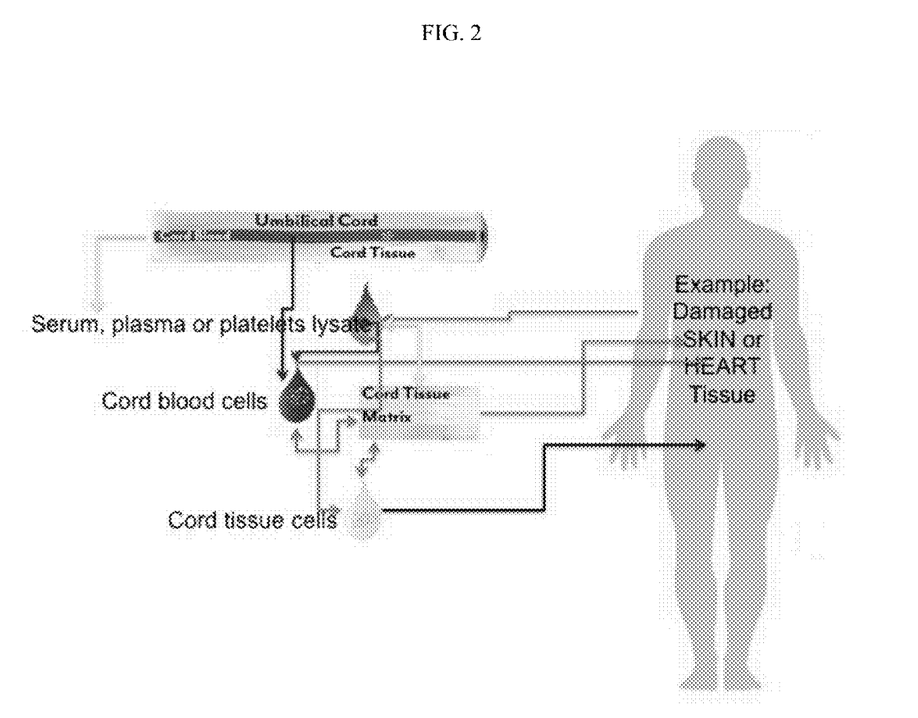
FIG. 2 is a schematic diagram illustrating possible uses of cord blood cells, cord tissue cells, cord matrices, or combination thereof to treat a degenerated tissue.
Figure 3:
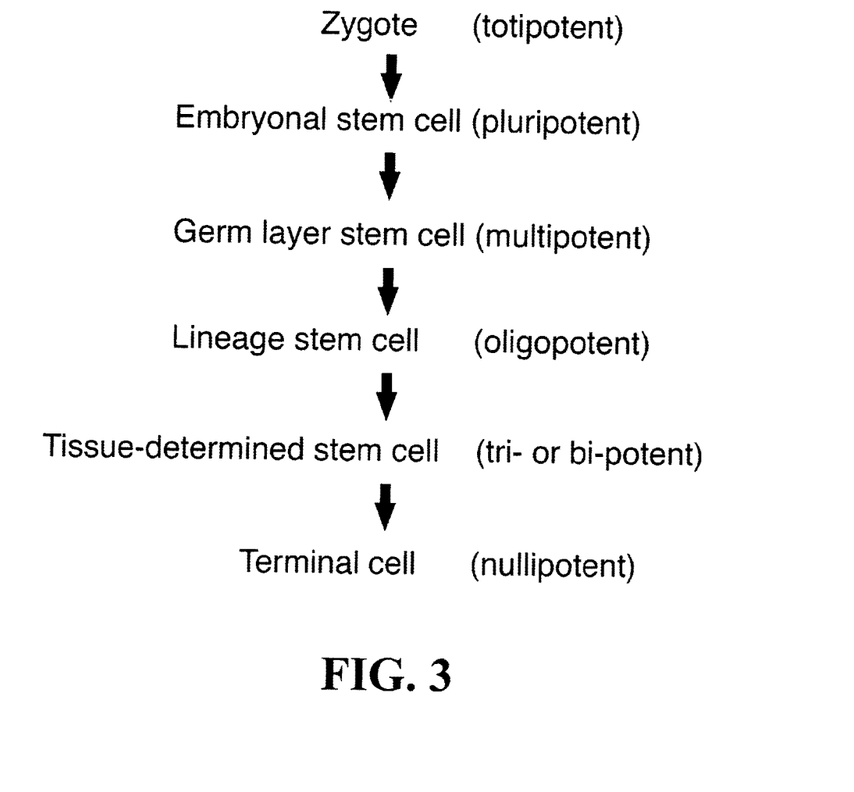
FIG. 3 is a schematic diagram illustrating the development process of cells.

On use, the cells can be reinfused back into tissue matrix of the desired shape. This is done by combining the two using a high concentration of cells and allowing the cells to diffuse into the matrix, or by injecting them thereinto, depending on matrix shape and size. Alternatively, the cells can be used as is, but the tissue matrix provides a useful scaffold and regulated environment for cell growth, and is a preferred methodology. Cells and tissues can be used alone or in any combinations for animal or human therapeutic purposes. See FIG. 1 and FIG. 2.

Although various embodiments of the method and apparatus of the present invention have been illustrated in the accompanying Drawings (FIGS. 1 and 2) and described in the foregoing Detailed Description, it will be understood that the invention is not limited to the embodiments disclosed, but is capable of numerous rearrangements, modifications and substitutions without departing from the spirit of the invention as set forth herein.

I claim:

1. A method, comprising:
   a) obtaining a first umbilical cord tissue from a first newborn animal;
   b) cleaning said first umbilical cord tissue with a sterilizing agent;
   c) mechanically dissociating said first umbilical cord tissue to isolate mixed cells from said first umbilical cord tissue without separating vessels from the rest of the cord tissue, wherein said cells are a mixture of differentiated cells, stem cells and progenitor cells;
   d) obtaining a second umbilical cord tissue from said first newborn animal or from a second newborn animal;
   e) cutting said second umbilical cord tissue to a desired shape without separating vessels from the rest of the cord tissue and treating said second umbilical cord tissue to produce a decellularized tissue;
   f) culturing said mixed cells together with said decellularized tissue such that said decellularized tissue provides a 3D scaffold for 3D culturing of said mixed cells, wherein said 3D culturing is in a 0.1% to 5% oxygen environment at 37° C. in a medium supplemented with serum, plasma or platelet lysate from said first newborn animal.

2. The method of claim 1, whereby said first umbilical cord tissue and said second umbilical cord tissue are from the same newborn animal.

3. The method of claim 1, wherein said dissociating step c) is by slicing or dicing said tissue with a blade.

4. The method of claim 1, wherein step e) is non-enzymatic.

5. The method of claim 1, where said 3D culturing step is performed in a humidified carbon dioxide cell culture chamber.

6. The method of claim 1, where said decellularized tissue and said mixed cells are stored together or separately at temperatures between −80° C. and −196° C. before use in said culturing step f).

7. The method of claim 1, where said decellularized tissue is lyophilized and stored at −80° C. before use in said culturing step f).

8. The method of claim 7, where said lyophilized decellularized tissue is thawed in phosphate buffer solution or water.

9. The method of claim 7, where said decellularized tissue is lyophilized and stored at room temperature before use in said 3D culturing step f).

10. The method of claim 9, where said lyophilized tissue matrix is reconstituted with water or phosphate buffer solution.

11. A method of producing stem cells, comprising:
    a) obtaining a first piece of umbilical cord from a newborn animal;
    b) cleaning said first piece of umbilical cord with a sterilizing agent;
    c) mechanically dissociating said first piece of umbilical cord to isolate mixed cells from said first piece of umbilical cord without separating vessels from the rest of the umbilical cord, wherein said mixed cells are a mixture of differentiated cells, stem cells and progenitor cells;
    d) obtaining a second piece of umbilical cord from said newborn animal;
    e) cutting said second piece of umbilical cord into a desired shape without separating vessels from the rest of the umbilical cord and treating said second piece of umbilical cord to produce a decellularized tissue;

f) culturing said mixed cells together with said decellularized tissue such that said decellularized tissue provides a 3D scaffold for 3D culturing of said cells, wherein said 3D culturing is in a 0.1% to 5% oxygen environment at 37° C. in a medium supplemented with serum, plasma or platelet lysate from cord blood from said newborn animal.

\* \* \* \* \*